United States Patent [19]

May

[11] 4,087,551

[45] May 2, 1978

[54] AMINO-BICYCLOHEPTANES

[75] Inventor: Peter John May, North Harrow, England

[73] Assignee: Glaxo Laboratories Limited, Greenford, England

[21] Appl. No.: 555,147

[22] Filed: Mar. 4, 1975

Related U.S. Application Data

[63] Continuation-in-part of Ser. No. 447,867, Mar. 4, 1974, abandoned.

[30] Foreign Application Priority Data

Mar. 6, 1973 United Kingdom .............. 10894/73
Mar. 6, 1973 United Kingdom .............. 10895/73

[51] Int. Cl.$^2$ .................... A61K 31/13; A61K 31/19; C07C 87/00
[52] U.S. Cl. ................ 424/325; 260/563 P; 424/317

[58] Field of Search ............ 260/563 P; 424/325, 424/317

[56] References Cited

U.S. PATENT DOCUMENTS 3,483,254  12/1969  Shen et al. .................. 260/563 P

OTHER PUBLICATIONS

Fisher, et al.–Chem. Abst., vol. 79, (1973), p. 18192e.
May–Chem. Abst., vol. 82, (1975), p. 16403n.

*Primary Examiner*—Sam Rosen
*Attorney, Agent, or Firm*—Bacon & Thomas

[57] ABSTRACT

Pharmaceutical compositions are described in which the active ingredient is a 7,7-dimethyl-[2,2,1]-bicycloheptane having at the 1-position a substituted or unsubstituted amino or aminomethyl group. The active ingredients have been found to possess antiviral and central nervous system activity.

15 Claims, No Drawings

AMINO-BICYCLOHEPTANES

This application is a continuation in part of my application Ser. No. 447,867 filed Mar. 4, 1974 now abandoned.

This invention relates to new bornane derivatives and to processes for their preparation, and in particular to 10-bornanamine and 7,7-dimethylnorbornan-1-amines and to derivatives thereof.

7,7-Dimethylnorbornan-1-amine (i.e. 1-amino-7,7-dimethyl-[2,2,1]-bicycloheptane) is a known compound and has the structure:

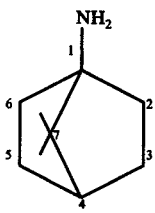

10-Bornanamine (i.e. 1-aminomethyl-7,7-dimethyl-[2,2,1]-bicycloheptane) is also a known compound and has the structure:

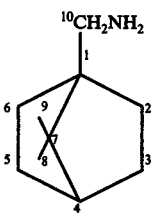

No pharmaceutical activity has previously been ascribed to these two compounds.

Antiviral activity of varying degrees has hitherto been shown in compounds having a wide variety of structures. Activity against rhino viruses in particular is not uncommon but activity against the more important influenza viruses is rare. In tests we have carried out we have surprisingly found good activity in the 10-bornanamine and 7,7-dimethylnorbornan-1-amine series against influenza viruses, particularly the H2N2 and H3N2 types, for example Iksha, Hong Kong 1/68 and England 42/72 strains.

We have for example found particularly interesting antiviral activity of this nature in 10-bornanamine and 7,7-dimethylnorbornan-1-amine and derivatives thereof having a basic nitrogen atom.

Compounds in these series are also of interest as regards central nervous system and cardiovascular activity, e.g. analgesic activity.

Thus in one aspect the invention provides a pharmaceutical composition comprising a pharmaceutical carrier or excipient and a 7,7-dimethyl-[2,2,1]-bicycloheptane having at the 1-position a group R, where R is an amino or aminomethyl group, or a derivative thereof possessing a basic nitrogen atom and/or a physiologically acceptable salt thereof, said derivative being a compound wherein R is substituted at the amino nitrogen atom and/or at the 10-carbon atom by one or more aliphatic, cycloaliphatic, araliphatic or aryl groups or, in the case of the amino group, by a heterocyclic group in which the nitrogen atom of the amino group forms part of the heterocyclic ring, or, in the case of an N-substituted aminomethyl group, by an oxo group at the 10-carbon atom.

The compounds just described in which R is substituted are themselves new compounds and constitute a further aspect of the invention.

The amino group may for example be mono- or disubstituted, such substituents generally having up to a total of 12 carbon atoms on the nitrogen atom.

Such aliphatic groups may be branched or straight chain, saturated or unsaturated, and substituted or unsubstituted. They preferably contain 1–6 carbon atoms and may for example be alkyl groups (e.g. methyl, ethyl, n-propyl and n-butyl), alkenyl groups (e.g. allyl), or alkynyl groups (e.g. propargyl). The aliphatic group may be joined to the nitrogen atom of the amino group by a double bond, as in the case of an alkylidene group, such as propylidene.

These aliphatic groups and particularly the alkyl groups may for example be substituted by amino, mono- or di-alkylamino, imino (e.g. as in amidino), hydroxy, etherified or esterified hydroxy (e.g. alkoxy or alkanoyloxy), thiol, or esterified or etherified thiol (e.g. alkylthio) groups.

When a basic substituent such as an amino group is present on the N-aliphatic substituent, an oxo group may be at the α-position in relation to the nitrogen atom of the R group, thus forming a basic substituted acylamino group, e.g. an aminoacetamido group. When R is a substituted aminomethyl group, the oxo group may be present at either α-position in relation to the nitrogen atom.

Cycloaliphatic substituents may for example be cycloalkyl groups having 3–8 or more (e.g. up to 10) carbon atoms such as cyclohexyl and 7,7-dimethylnorbornan-1-yl.

Araliphatic substituents may for example be monocyclic aralkyl, aralkenyl or aralkynyl groups such as benzyl, styryl and phenylethynyl groups. The aliphatic group may be joined to the nitrogen atom of the amino group by a double bond as for example in a benzylidene group. The aliphatic portions of such araliphatic groups preferably contain 1–6 carbon atoms.

Aryl substituents may for example be monocyclic aryl groups such as phenyl, or heterocyclic aryl groups containing for example 5 or 6 ring members and having one or more hetero atoms, e.g. N, O or S.

Substituted amino groups in which the amino nitrogen atom forms part of a heterocyclic ring may for example be saturated or unsaturated, contain 4–8, preferably 5 or 6, ring members and they may contain another (e.g. a second) hetero atom such as N, O or S. Examples of such groups are piperidino, morpholino, thiomorpholino, pyrrolidino, azetidino and piperazino groups. The heterocyclic ring may itself be substituted, for example by hydroxy or alkyl groups, such as a methyl group, as in a 4-methylpiperazino group, or a hydroxy group, as in a 3-hydroxyazetidino group. The heterocyclic ring may also be fused to a second ring, e.g. a benzene ring, as in an isoindolino group.

The heterocyclic ring may also be substituted by a cycloalkyl group such as described above, as for example in 1,3,5-tris-(bornan-10-yl)-hexahydro-1,3,5-triazine.

Thus, the amino group which is present in the R group of the compounds used in the invention may be of the formula $-NR^1R^2$ wherein $R^1$ and $R^2$, which may be the same or different are hydrogen atoms or aliphatic, cycloaliphatic, araliphatic or aryl groups as described above, or wherein $R^1$ and $R^2$ are taken together with the intervening nitrogen atom represent a heterocyclic ring as described above, or wherein $R^1$ and $R^2$ taken together represent a divalent aliphatic or araliphatic group.

When R is an aminomethyl group, either or both of the hydrogen atoms on the 10-carbon atom may be replaced by a substituent which may, for example, be an aliphatic, cycloaliphatic, araliphatic or aryl (particularly phenyl) substituent such as generally referred to above. There may in particular be one or two $C_{1-6}$ alkyl substituents such as methyl or ethyl groups. When the 10-carbon atom is substituted, the amino group will usually but not necessarily be unsubstituted.

Acid addition salts and especially physiologically acceptable acid addition salts are also included in the invention, examples of such salts being hydrochlorides, hydrobromides, phosphates, sulphates, p-toluene sulphonates, methane sulphonates, citrates, tartrates, acetates, ascorbates, lactates, maleates, and succinates.

Compounds which are generally preferred for use in accordance with the invention are those in which R is an amino, mono- or di-alkylamino aminomethyl, mono- or dialkylaminomethyl, mono- or di-alkenylaminomethyl, or 1-aminoethyl group, or a group (particularly an aminomethyl group) in which the nitrogen atom forms part of a saturated 5 or 6 membered heterocyclic ring which may contain a second hetero atom, or one or more substituents, or is fused to a second (e.g. benzene) ring. More preferably, the alkyl groups have 1-4 carbon atoms, and especially are methyl or ethyl groups.

Specific compounds which are particularly preferred on account of their antiviral activity are those in which R is an aminomethyl group or the monomethyl, monoethyl, dimethyl, diethyl monoallyl or mono-n-butyl amino substituted derivatives thereof, or a 4-methylpiperazinomethyl, piperidinomethyl, isoindolinomethyl or morpholinomethyl group; a 1-aminoethyl group; or an amino, methylamino, ethylamino or dimethylamino group.

In tissue culture tests which we have carried out, compounds in which R is aminomethyl, mono- or dimethylaminomethyl, mono- or di-ethylaminomethyl, mono-n-butylaminomethyl, N-methylpiperazinomethyl, piperidinomethyl, morpholinomethyl, isoindolinomethyl, 1-aminoethyl, amino, or monomethylamino have shown high activity against the Iksha strain of the influenza $H_2N_2$ virus.

The compounds in which R is aminomethyl, mono- and di-ethylaminomethyl, mono-n-butylaminomethyl, N-methylpiperazinomethyl, allylaminomethyl, 1-aminoethyl, amino, mono- or di-methylamino or ethylamino have shown high activity against the England 42/72 strain of the influenza $H_3N_2$ virus.

Tests we have carried out in mice have shown that certain of the compounds have protection against the influenza England 42/72 H3N2 virus when administered orally. These compounds are particularly preferred, and are those in which R is an aminomethyl group or the methyl, ethyl or dimethyl amino-substituted derivatives thereof, or a 1-aminoethyl, dimethylamino, or morpholinomethyl group. The diethylaminomethyl, 4-methylpiperazinomethyl or isoindolinomethyl compounds have been found to give protection when administered intraperitoneally to mice.

As indicated above, many of the compounds in accordance with the invention have additionally shown central nervous system activity in our animal tests, particularly anti-nicotine tests, and the results indicate that these compounds are of interest in the treatment of conditions in which there is an imbalance between cholinergic and dopaminergic activity in the nervous system such as Parkinsons Disease.

Compounds in which R is an amino or aminomethyl group or such groups substituted at the nitrogen atom by one or two $C_{1-4}$ alkyl groups are particularly preferred in this respect, especially compounds in which R is an amino or mono- or di-$(C_{1-4})$alkylamino group, for example methylamino, ethylamino and dimethylamino.

The physiologically active compounds of the invention may be formulated for administration in conjunction, if desired, with one or more pharmaceutical (including veterinary) carriers or excipients or other medicinal agents suitable, for example, for oral, topical, rectal, or parenteral administration.

They may be used together with other medicinal agents for example antiinflammatory agents such as steroids, e.g., betamethasone 21-phosphate or antibiotics such as tetracycline. The compositions are conveniently in dosage unit form and each dosage unit should generally contain above 0.025g, e.g. 0.05 to 4g and preferably 0.1 to 1.0g, of the active compound, for administration 1-3 times daily generally or, for intranasal or inhalation administration, e.g. 6-8 times daily. The total daily dose should generally be above 0.05g, e.g. from 0.10 to 7g. The carrier or excipient will in general be a solid carrier or excipient, a sterile liquid or a liquid containing one or more stabilising, flavouring, suspending, sweetening, emulsifying or preserving agents.

When the composition is in the form of an aerosol, it should be such that each spray provides approximately 1/20 to 1/40 th of the dosage unit amounts given above. The total daily dose will usually be about ⅛ th of that referred to above.

The dosages mentioned above are applicable to the use of the compounds on account of their antiviral activity. For use on account of their central nervous system activity, the compounds should be formulated so as to provide 5-500 mg per day, preferably 10-100 mg, conveniently as a single dose in the form of tablets or capsules.

The dosages referred to above are those for an adult human (bodyweight approximately 70kg) and may of course be varied for children or animals according to body weight.

Solid preparations for oral consumption are usually presented in unit dose form and include for instance, tablets, capsules, lozenges, chewing gum and medicated sweets. Conventional carriers for such preparations may be sugars, starches, sugar alcohols, gelatin, chicle gum, cocoa butter, etc., together with other compounding agents required such as binders, lubricants, stabilisers, coatings, flavourings and colourings. The compositions may also take the form of liquid oral preparations for ingestion such as solutions, suspensions, syrups, elixirs, emulsions, granules for re-constitution before use, which may contain suspending, emulsifying, stabilising and preserving agents and may also contain acceptable sweetening, flavouring or colouring agents. The compounds may be prepared for local application to the mucous membranes of the nose and throat and may take the form of liquid sprays, aerosols or powder insufflations, nasal drops or ointments, throat paints, gargles or similar preparations. Topical formulations for the treatment of eyes may be prepared in oily or aqueous media in the form of conventional ophthalmic preparations and collyria, for example creams, ointments, eye drops and lotions. Suppositories may contain a conventional base e.g. oil of theobroma, polyglycols, together with surface active agents if required. The injectable preparations may take the form of aqueous or oily solutions, emulsions, suspensions or solids for reconstitution before use. Suitable vehicles include, for example, sterile, pyrogen-free water, parenterally acceptable oils, oily esters or other non-aqueous media such as propylene glycol, if desired containing suspending, dispersing, stabilising, preserving, solubilising, emulsifying or buffering agents.

Particularly suitable forms of administration are tablets, solutions for injection, nasal sprays or drops, sprays for the respiratory tract, e.g. aerosols for inhalation.

Compounds in accordance with the invention which possess a methylene group in an α-position in relation to the nitrogen atom of the R group may be prepared by reduction of a corresponding amide.

This reaction may for example be carried out with a hydride reagent capable of reducing amides to amines, such as lithium aluminium hydride or diborane, in an inert organic solvent, for example a hydrocarbon solvent such as benzene or toluene or an ether solvent such as diethyl ether or tetrahydrofuran. The reaction with lithium aluminium hydride is suitably carried out at the reflux temperature of the reaction mixture, although lower temperatures may if desired be used. The reaction with diborane may for example be effected at temperatures of $-10$ to $+30°$ C, conveniently at room temperature. The amine produced is conveniently isolated in the form of a salt, e.g. the hydrochloride.

Thus for example amino compounds having a araliphatic substituent or an aliphatic substituent may for example be prepared by reducing the corresponding substituted amide compound (i.e. a compound where R is an acylamino or acylaminomethyl group).

The amides required as starting materials for the latter reaction are readily obtainable by acylation of the parent amino compound, e.g. with an acid halide corresponding to the desired substituent. This reaction is desirably effected in the presence of an acid binding agent and suitable basic conditions may be provided by using an excess of the starting amino compound, but preferably in the presence of added base.

Compounds in accordance with the invention wherein R is a substituted aminomethyl group (e.g. compounds having a 1-substituent of the formula $-CH_2NR^1R^2$) may conveniently be prepared by reduction of the corresponding 7,7-dimethyl-norbornane-1-carbonamide.

The 1-carbonamides used as starting materials in the preparation of the aminomethyl compounds are new and constitute a further aspect of the invention. The invention thus includes N-substituted 7,7-dimethyl-norbornane-1-carbonamides. The N-substituents may of course be the same as those described above with reference to the amino substituted 10-bornanamines.

As indicated above, it will be appreciated that in addition to their utility as intermediates in the preparation of the 10-bornanamines of the invention certain of these amides also possess antiviral activity similar to that of the amines. These are amides in which the N-substituent itself bears a basic substituent, for example an aliphatic substituent, such as an alkyl group, substituted by an amino group. An example of such a compound is the compound in which R is a 4-methyl-piperazinocarbonyl group.

The 1-carbonamides may be prepared, for example, by reaction of 7,7-dimethyl-norbornane-1-carboxylic acid or preferably a reactive derivative thereof such as a halide (e.g. 7,7-dimethyl-norbornane-1-carbonyl chloride) with a primary or secondary amine corresponding to the mono- or disubstituted amino group of the desired amide.

This reaction is desirably carried out at a low temperature (e.g. $-80°$ C to $10°$ C) in the presence of an acid binding agent (e.g. a base). These basic conditions can also be provided by the use of an excess of the amine. The reaction is conveniently carried out in a non-polar organic solvent such as an ether solvent, e.g. diethyl ether.

The 7,7-dimethyl-norbornane-1-carbonyl chloride preferably used in the latter reaction is a known compound and is readily prepared from 7,7-dimethyl-norbornane-1-carboxylic acid.

Compounds according to the invention containing a monomethylamino substituent may be prepared for example by reduction of an ester of the corresponding carboxyamino compound. The ester is suitably an alkoxy carbonylamino compound.

The reduction is desirably effected with a hydride reducing agent, preferably lithium aluminium hydride, in for example an ether solvent such as diethyl ether. The reaction is preferably carried out at the reflux temperature of the medium. The amine produced is conveniently isolated as a salt by the addition of acid, e.g. hydrochloric acid.

Methylamino compounds may also be prepared by methylation (e.g. reductive methylation with formaldehyde in the presence of formic acid or sodium borohydride) of the parent amine.

Compounds in accordance with the invention wherein the nitrogen atom of the amine group is joined by a double bond to an aliphatic or araliphatic substituent may be prepared by condensing the unsubstituted amino compound (which may be in the form of a salt) with an aldehyde or ketone (e.g. acetone or benzaldehyde) in a suitable medium preferably with azeotropic removal of water, e.g. using toluene or benzene or a chlorinated hydrocarbon as solvent. The use of formaldehyde in this reaction results in the preparation of the previously mentioned triazine.

Compounds wherein R is an aminomethyl group wherein one of the hydrogen atoms on the methyl carbon atom is replaced by a substituent and the amino group is unsubstituted may be prepared by reduction of the corresponding 10-hydroxyimino (ketoxime) bornane. This reduction may for example be effected by hydrogenation over a nickel catalyst, or by reduction with zinc and acetic acid, lithium aluminium hydride, or sodium in the presence of a lower alkanol, e.g. ethanol.

The 10-hydroxyimino compound required as the starting material in the above reaction may be prepared by condensing the corresponding ketone (i.e. a compound of formula II above having at the 1-position the group $-COR^3$ where $R^3$ is the desired 10-substituent) with hydroxylamine. This reaction is conveniently carried out in an aqueous medium and preferably at the reflux temperature of the medium. The hydroxylamine is normally used in the form of a salt e.g. sulphate or hydrochloride, in the presence of a base.

The ketones required for the latter reaction may for example be prepared from 7,7-dimethyl-norbornane-1-carboxylic acid by reaction with a metal (e.g. lithium) derivative of the formula $MR^4$ where M is the metal and R[4] is the desired hydrocarbon substituent in the 10-position.

The amino compounds having an aryl substituent may for example be prepared by treating the parent amino compound (e.g. in the form of a salt, e.g. a lithium salt) with a benzyne. The benzyne required for this reaction may suitably be prepared by reaction of an aryl halide (e.g. chloride or bromide) with an excess of the lithium salt of the parent amino compound.

Compounds wherein the amino group is substituted by an aliphatic, cycloaliphatic or araliphatic group may also be prepared by reaction of the parent amine with a compound of the formula $R^5X$ where $R^5$ is the desired substituent and X is a readily eliminatable group, such as a halogen (e.g. chlorine) atom or a toluene sulphonyloxy group. This reaction may be carried out in a polar solvent (such as dimethylformamide) or acetone, in the presence of a base (e.g. sodium hydride), preferably using an excess of the amine. The reaction is particularly applicable to the preparation of disubstituted amines, but it may also be used to prepare mono-substituted compounds. Alternatively, the use of this reaction of an epoxide affords a method of preparing hydroxyalkylamino compounds.

Compounds wherein the amino nitrogen atom is a member of a heterocyclic ring may be prepared by cyclisation of such hydroxyalkylamino compounds carrying a group capable of elimination. Such a product may be obtained for example by reacting the amine with epichlorhydrin. The cyclisation may for example be effected by heating the starting materials in solution.

Compounds wherein R is an aminomethyl group and the 10-carbon atom is substituted may be prepared by reduction of the corresponding nitro methyl compound. The reduction may be effected for example with a hydride reducing agent (such as lithium aluminium hydride or diborane). The reaction is generally suitable for the preparation of compounds wherein R is —$CR^5R^6NH_2$, where $R^5$ has the above meaning and $R^6$ is hydrogen or an aliphatic, cycloaliphatic or araliphatic group; it is preferred that $R^5$ is lower alkyl e.g. methyl and $R^6$ is hydrogen or lower alkyl, e.g. methyl. More preferably $R^5$ and $R^6$ are both methyl.

The nitro derivatives required for the latter reaction may be prepared by reacting a compound of the formula $R^5X$ with a corresponding nitro compound in which the carbon atom of the R group is unsubstituted or monosubstituted (i.e. a compound where R is —$CHR^6NO_2$ where $R^6$ has the above meaning). The conditions for this reaction are generally similar to those described above with regard to the reaction of $R^5X$ with an amine, and are desirably anhydrous. A strong base such as an alkali metal hydride is advantageously present in order to form the reacting species, which is a nitronic acid anion.

The monosubstituted or unsubstituted nitro compounds may themselves be prepared by oxidation of a corresponding amine or ketoxime (i.e. a compound in which R is —$CHR^6NH_2$ or —$CR^6=NOH$). The oxidation may be effected for example with a peracid (e.g. m-chloroperbenzoic or per-trifluoracetic) in a hydrocarbon or chlorinated hydrocarbon solvent, preferably at room temperature. The preparation of suitable ketoximes is described above.

Compounds in which the nitrogen atom of R is substituted by an aminoacyl or mono- or di-alkylaminoacyl group may be prepared by reaction of the corresponding haloacyl (e.g. bromoacyl) compound with ammonia or a mono- or dialkylamine. A suitable solvent for this reaction is an alcohol, e.g. methanol. An excess of ammonia is preferable.

Compounds in which the nitrogen atom of R is substituted by a haloacyl group in which the halogen atom is separated from the carbonyl group by at least 2 carbon atoms may be subjected to cyclisation to yield a corresponding lactam; the cyclic amide grouping can then be reduced to give a basic compound according to the invention. The cyclisation may be effected under basic conditions, e.g. using sodium hydride in a polar aprotic solvent such as dimethylsulphoxide. The reduction of the cyclic amide group may, for example, be effected using a hydride reducing agent such as lithium aluminium hydride or diborane.

Compounds wherein the amino nitrogen atom is a member of a heterocyclic ring may also be prepared by reaction of the parent amine with a compound possessing two readily eliminatable groups such as referred to above. The latter compound may for example be of the formula $XR^7X$ where X is as defined above and $R^7$ is a divalent alkylene group (which may be interrupted by an oxygen or sulphur atom) or a cyclic group bearing two monovalent alkylene groups (e.g. an o-xylenyl group). The reaction may be performed for example as described above for the reaction of $R^5X$ with an amine.

Compounds possessing an amino group substituted by an aliphatic or araliphatic group may also be prepared by reduction of the corresponding compound in which the amino nitrogen atom is linked to the substituent by a double bond. The reduction may for example be effected with a metal hydride, for example as described above.

The following Examples illustrate the invention. Temperatures are in ° C.

EXAMPLES 1–8

Preparation of the 7,7-dimethyl-norbornane-1-carbonamides

The eight amides whose properties are summarised in Table I below were prepared by the following general method. Variations on the method are noted in the footnote to the Table.

A solution of freshly prepared 7,7-dimethyl-norbornane-1-carbonyl-chloride:
(10 mmoles) in dry ether (usually about 10 ml.) was cooled in an ice-bath and stirred whilst the appropriate amine (2 equivalents) was added dropwise over 5–10 minutes. When the addition was complete the mixture was allowed to come to room temperature. After 1–2 hours the reaction mixture was partitioned between chloroform and dilute hydrochloric acid and the organic extract washed with dilute sodium carbonate and water and then dried over magnesium sulphate. Evaporation of the organic solvent afforded the crude amide which was purified by sublimation at about 0.1 mm and/or crystallisation.

Table 1

7,7-Dimethyl-norbornane-1-carbonamides

| Amide Example No. | X | M.P. °C (Kofler) | Empirical Formula | C Found | C Req. | H Found | H Req. | N Found | N Req. |
|---|---|---|---|---|---|---|---|---|---|
| 1 | NHMe[1] | 116–117[2] | $C_{11}H_{19}NO$ | 72.85 | 72.9 | 10.8 | 10.55 | 7.5 | 7.75 |
| 2 | NHEt | 113–114.5[3] | $C_{12}H_{21}NO$ | 73.4 | 73.8 | 10.5 | 10.8 | 7.1 | 7.2 |
| 3 | NHBu | 72.5–73.5 | $C_{14}H_{25}NO$ | | | | | | |
| 4 | NMe$_2$[4] | 91–92[5] | $C_{12}H_{21}NO$ | 73.4 | 73.8 | 10.6 | 10.8 | 6.9 | 7.2 |
| 5 | NEt$_2$ | 38–40[6] | $C_{14}H_{25}NO$ | 75.0 | 75.3 | 11.2 | 11.3 | 6.05 | 6.3 |
| 6 | (piperidino) | 52–54 | $C_{15}H_{25}NO$ | | | | | | |
| 7 | (morpholino) | 117–118 | $C_{14}H_{23}NO_2$ | 70.5 | 70.9 | 9.85 | 9.8 | 5.75 | 5.9 |
| 8 | (N-methylpiperazino)[7] | 113–114 | $C_{15}H_{26}N_2O$ | 71.6 | 71.9 | 10.2 | 10.5 | 11.2 | 11.2 |

Footnotes to Table 1

[1] The acid chloride (25 mmoles), in ether (25 ml.), was stirred at −70° whilst a large excess (10 ml.) of liquid methylamine was added.
[2] After crystallization from ether.
[3] The crude amide was purified by chromatography over silica before sublimation and crystallization from petroleum ether.
[4] Reaction mixture was allowed to stand at room temperature for 1 week.
[5] After crystallization from petroleum ether.
[6] The crude amide was purified by chromatography over silica before sublimation.
[7] The reaction mixture was partitioned between chloroform and dilute hydrochloric acid and the aqueous layer basified with sodium carbonate and extracted with chloroform. Evaporation of the organic solvent afforded a solid which was purified by sublimation.

EXAMPLES 9–16

Eight 10-bornanamines were prepared by the following general method and their properties summarised in Table 2. Variations on the method are given in the footnote to the Table.

A solution of the appropriate amide in the chosen solvent (see Table 2) was carefully added to a suspension of an excess of lithium aluminium hydride in the same solvent and the resulting mixture refluxed until the reaction, as judged by thin-layer chromatography, was complete. The excess lithium aluminium hydride was destroyed by the careful addition of water, more benzene (or ether or chloroform) was added and the insoluble inorganic material removed by filtration. The organic layer was washed with water, dried (MgSO$_4$) and evaporated in vacuo. The residual crude amine was dissolved in ether, approx. 8N-ethanolic hydrogen chloride was added and the precipitated amine hydrochloride collected by filtration and dried.

Table 2

10-Bornanamine Hydrochlorides

| Amine Ex. No. | R | Reduction Solvent | sublimation Point °C Kofler | Empirical Formula | C Found | C Req. | H Found | H Req. | Cl Found | Cl Req. | N Found | N Req. |
|---|---|---|---|---|---|---|---|---|---|---|---|---|
| 9 | NHMe | Tetrahydrofuran | 259 | $C_{11}H_{22}ClN$ | 64.3 | 64.85 | 10.5 | 10.9 | 17.3 | 17.4 | 6.9 | 6.9 |
| 10 | NHEt | Benzene[1] | 285[2] | $C_{12}H_{24}ClN$ | 66.5 | 66.2 | 11.3 | 11.1 | 15.4 | 16.3 | 6.0 | 6.4 |
| 11 | NHBu | Tetrahydrofuran[3] | 287[4] | $C_{14}H_{28}ClN$ | 68.05 | 68.4 | 11.55 | 11.5 | 14.4 | 14.4 | 5.55 | 5.7 |
| 12 | NMe$_2$ | Tetrahydrofuran | 245 | $C_{12}H_{24}ClN$ | | | | | | | | |
| 13 | NEt$_2$ | Benzene | 284 | $C_{14}H_{28}ClN$ | 68.25 | 68.4 | 11.55 | 11.5 | 14.4 | 14.4 | 5.55 | 5.7 |

Table 2-continued

10-Bornanamine Hydrochlorides

| Amine Ex. No. | R | Reduction Solvent | sublimation Point °C Kofler | Empirical Formula | C Found | C Req. | H Found | H Req. | Cl Found | Cl Req. | N Found | N Req. |
|---|---|---|---|---|---|---|---|---|---|---|---|---|
| 14 | (piperidinyl-CH₂-) | Tetrahydrofuran[3] | 259° [5] | $C_{15}H_{28}ClN$ | 69.4 | 69.85 | 10.7 | 10.95 | 13.75 | 13.75 | 5.2 | 5.45 |
| 15 | (morpholinyl-CH₂-) | Tetrahydrofuran | 248 | $C_{14}H_{26}ClNO$ | 64.6 | 64.7 | 10.15 | 10.1 | 13.7 | 13.65 | 5.45 | 5.4 |
| 16 | (N-methylpiperazinyl-CH₂-) | Benzene | 252–254[6] | $C_{15}H_{30}Cl_2N_2 \cdot 2H_2O$ | 51.7 | 52.15 | 9.6 | 9.9 | — | — | 8.0 | 8.1 |

Footnotes to Table 2
[1]After destruction of the excess hydride and removal of the inorganic material the benzene solution was extracted with dilute hydrochloric acid. Basification of the acid solution and extraction with chloroform gave the crude amine as an oil which was converted into its hydrochloride.
[2]Change of crystalline form about 170°.
[3]After destruction of the excess hydride and removal of the inorganic material the reaction mixture was partitioned between chloroform and dilute hydrochloric acid. Basification of the acid solution and extraction with chloroform gave the crude amine which was converted into its hydrochloride.
[4]Change in crystalline form at about 220°.
[5]After crystallization from chloroform.
[6]The crude amine was purified by preparative thin-layer chromatography over silica, converted to its dihydrochloride and crystallized from ethanol.

EXAMPLE 17

1-(1′-Aminoethyl)-7,7-dimethyl-norbornane hydrochloride (i) 7,7-Dimethylnorbornyl-1-methyl ketone oxime A solution of 7,7-dimethylnorbornane-1-carboxylic acid (2.54 g.) in ether (60 ml) was treated dropwise, under nitrogen, with a 2M-solution of methyl lithium in ether (24 ml). When the addition was complete the mixture was refluxed for 2.5 hours. The cooled solution was washed with 2N-hydrochloric acid, sodium carbonate solution and water and then dried over sodium sulphate. Evaporation of the ether afforded 7,7-dimethylnorbornyl-1-methyl ketone as a pale yellow oil (2.49 g.) $\nu_{max}$(in CHBr₃) 1682 cm⁻¹. This oil (2.42 g.) in ethanol (60 ml) was treated with hydroxylamine hydrochloride (1.29 g.) and N-sodium hydroxide solution (63 ml) and the mixture, after being kept overnight at room temperature, was refluxed for 0.5 hours. The cooled reaction mixture was extracted with chloroform, the extracts washed with water and dried (Na₂SO₄) and the solvent removed in vacuo to afford the crude crystalline product (2.65 g.) which was recrystallized from aqueous ethanol to give title compound m.p. 109° – 111° (kofler).

A similar sample, m.p. 109.5° – 110.5° (kofler) had C, 73.05; H, 10.7; N, 7.4; $C_{11}H_{19}NO$ requires C, 72.9; H, 10.55; N, 7.75%.

(ii) 1-(1′-Aminoethyl)-7,7-dimethyl norbornane hydrochloride

A solution of 7,7-dimethylnorbornyl-1-methyl ketone oxime (253 mg) in ethanol (20 ml) containing Raney nickel catalyst was shaken with hydrogen for 22 hours. The catalyst was removed by filtration and the solution evaporated in vacuo to give an oil which was partitioned between chloroform and water. The chloroform layer was extracted with 2N-hydrochloric acid (50 ml) and after basification with sodium carbonate solution was extracted with chloroform. The organic extract was washed with water, dried (MgSO₄) and evaporated to give a yellow oil. This oil was dissolved in ether, ethanolic hydrogen chloride was added and the precipitate collected by filtration to give title compound, which sublimes at about 263° (Kofler).

EXAMPLE 18

1-Methylamino-7,7-dimethyl-norbornane hydrochloride

A solution of 1-(methoxycarbonylamino)-7,7-dimethylnorbornane (197 mg.) in ether (5 ml) was added to a suspension of lithium aluminium hydride (80 mg.) in ether (5 ml.) and the resulting mixture refluxed for three hours. Excess lithium aluminium hydride was decomposed by the addition of water and the precipitated inorganic material removed by filtration. The ethereal solution was washed with water, dried (MgSO₄) and the solvent evaporated. Treatment of the residual oil, in ether, with 8N-ethanolic hydrogen chloride afforded 1-methylamino-7,7-dimethyl-norbornane hydrochloride, sublimation point 260° (Kofler) (Found: C, 63.1; H, 10.4; Cl, 18.7; N, 7.4. $C_{10}H_{20}ClN$ requires C, 63.3; H, 10.65; Cl, 18.7; N, 7.4%).

EXAMPLE 19

1-Ethylamino-7,7-dimethylnorbornane hydrochloride

A solution of 1-amino-7,7-dimethylnorbornane (1.022 g) in pyridine (10 ml) was cooled in an ice-bath and stirred whilst acetyl chloride (1 ml) was added dropwise. The ice-bath was removed and the mixture was kept at room temperature until the reaction was complete. Dilution with water, acidification with dilute hydrochloric acid and extraction with ether afforded the crude product which was purified by filtration through a small column of neutral alumina and crystallization from ether-petroleum ether to give 1-acetamido-7,7-dimethylnorbornane m.p. 133°–134° (Kofler) after previous softening.

The above N-acetyl compound (776 mg) in dry ether (25 ml) was added to a mixture of lithium aluminium hydride (1 g) in ether (75 ml) and the mixture refluxed for two hours. Excess reagent was destroyed by the addition of water (5 ml) and the precipitated material removed by filtration. Extraction of the filtrate with ether afforded the crude ethyl amino compound which was dissolved in ether and treated with ethanolic hydrogen chloride. The insoluble amine hydrochloride was collected by filtration and crystallized from ethanol-ether to yield title compound; sublimes above 150°.

Found: C, 65.0; H, 11.0; N, 6.95; Cl, 17.4 $C_{11}H_{22}ClN$ requires: C, 64.85; H, 10.9; N, 6.85; Cl 17.4%.

EXAMPLE 20

10-Allylamino bornane hydrobromide and 10-diallylamino bornane hydrochloride

A mixture of 10-bornanamine (1 g.) sodium hydride (0.16 g.) and dimethyl formamide was stirred for 15 min. It was then cooled in an ice bath and allyl bromide (0.55 ml) was added. The mixture was stirred for 2 hours at room temperature and then partitioned between ether and water. The organic layer was dried ($MgSO_4$) and evaporated. The residue (1.04 g.) was subjected to preparative layer chromatography using a mixture of 5% methanol in chloroform for development of the plates. The more polar fraction (0.6 g) was dissolved in dry ether and treated with hydrogen chloride to give 10-allylamino bornane hydrobromide (0.65 g.).

The less polar fraction (0.34g.) was dissolved in dry ether and treated with hydrogen chloride to give 10-diallylamino bornane hydrochloride (0.25g.), mp. 163°-164°, (Found: C, 70.3; H, 10.7; Cl, 13.2; N, 5.2. $C_{16}H_{28}ClN.\frac{1}{4} H_2O$ requires C, 70.0; H, 10.65; Cl, 12.9; N, 5.1%).

EXAMPLE 21

(i) 10-Bromoacetamido bornane

10-Bornanamine (0.5 g) in dry ether (30 ml) containing pyridine (C.45 ml) was treated at −80° with a solution of bromoacetyl bromide (0.3 ml) in ether (5 ml) over one minute with stirring. The mixture was allowed to warm to room temperature and after a further 30 min. it was partitioned between ether and water. The organic layer was washed with 2N-hydrochloric acid solution and then water. It was dried ($MgSO_4$) and evaporated. The residue (0.73 g.) was purified by preparative layer chromatography and by crystallisation from petroleum ether (bp. 60°-80°) to give the title compound (0.48 g) mp. 89°, (Found: C, 52.4; H, 7.3; Br, 28.9; N, 5.0; $C_{12}H_{20}BrNO$ requires C, 52.55; H, 7.35; Br, 29.1; N,5.1%).

(ii) 10-Aminoacetamido-bornane hydrochloride

10-Bromoacetamido bornane (0.36 g.) was added to a 15% solution of ammonia in methanol (10 ml) and allowed to stand at room temperature for 20 hr. The mixture was then evaporated and the residue partitioned between 2N-hydrochloric acid solution and ether. The aqueous layer was basified with sodium hydroxide and extracted into ether. The organic extract was washed with water, dried ($MgSO_4$) and evaporated. The residue (0.18g) was dissolved in dry ether and treated with hydrogen chloride to give the title compound (0.19 g.) mp. 233°-235° (Found: C, 57.5; H, 9.2; Cl, 13.6; N, 11.2. $C_{12}H_{23}ClN_2O.\frac{1}{4} H_2O$ requires C, 57.35; H, 9.4; Cl, 14.1; N, 11.15%).

EXAMPLE 22

(i) 1-Bromoacetamido-7,7-dimethyl-norbornane

1-Amino-7,7-dimethyl-norbornane (1 g.) in dry ether (50 ml) containing pyridine (1 ml) was treated at −80° with a solution of bromoacetyl bromide (0.7 ml) in ether (10 ml.). The mixture was then allowed to warm to room temperature and stirred for 1 hr. It was then partitioned between ether and 2N-hydrochloric acid solution. The organic layer was washed with water, dried ($MgSO_4$) and evaporated. The residue (1.48 g) was crystallised from petroleum ether (bp. 60°-80°) to give the title compound (1.35 g) mp. 97°-98° (Found: C, 51.0; H, 7.1; Br, 30.5; N, 5.2, $C_{11}H_{18}BrNO$ requires C, 50.8; H, 7.0; Br, 30.7; N, 5.4%).

(ii) 1-Aminoacetamido-7,7-dimethyl-norbornane hydrochloride

1-Bromoacetylamino-7,7-dimethyl-norbornane (1.12 g) was added to a 15% solution of ammonia in methanol (50 ml) and allowed to stand at room temperature for 20 hr. The mixture was then evaporated and the residue partitioned between ether and water. The organic layer was dried ($MgSO_4$) and evaporated. The residue (0.43 g) was dissolved in dry ether and treated with hydrogen chloride to give the title compound (0.44 g) mp. 179°-182°, (Found: C, 55.8; H, 9.1; Cl, 15.1; N, 11.9 $C_{11}H_{21}ClN_2O. \frac{1}{4}H_2O$ requires C,55.7; H,9.1; Cl,14.9; N,11.8%).

EXAMPLE 23

N-Ethyl-10bornanamine hydrochloride

A solution of boron trifluoride etherate (5.75ml) in dry tetrahydrofuran (5ml) was added dropwise over a period of 5 min. to a stirred mixture of sodium borohydride (1.14g.) in dry tetrahydrofuran (18ml.) at −10°. The mixture was allowed to stir at room temperature for 1.hr. and then a solution of N-ethyl-7,7-dimethylnorbornane-1-carbonamide (0.5g) in dry tetrahydrofuran (5ml) was added. After a further 20 hr. the mixture was added to iced water (50ml). Concentrated hydrochloric acid (10ml) was added and the mixture was heated under reflux for 30 min. It was then cooled and partitioned between ether and dilute sodium hydroxide solution. The organic layer was washed with water, dried ($MgSO_4$) and evaporated. The residue was dissolved in dry ether and treated with hydrogen chloride to give the title compound (0.5g). Sublimes above 285°.

EXAMPLE 24

1-(1′-Aminoethyl)-7,7-dimethylnorbornane hydrochloride

A boiling solution of 7,7-dimethylnorborn-1-yl methyl ketone oxime (2.9g) in absolute ethanol (100ml) was treated with sodium (8g). When all of the sodium had reacted the mixture was cooled and partitioned between ether and water. The organic layer was dried ($MgSO_4$) and evaporated. The residue (1.89g) was dissolved in dry ether and treated with hydrogen chloride to give the title compound (2.16g.). Sublimes above 260°.

EXAMPLE 25

N-(10-Bornyl) isoindoline hydrochloride

A solution of 10-bornanamine (1.274g) in dimethylformamide (10ml) containing triethylamine (2.31ml) was cooled in ice and stirred whilst a solution of α,α'-dibromo-o-xylene (2.195g) in dimethylformamide (5ml) was added. The mixture was kept at room temperature for 24 hours and then diluted with water and extracted several times with chloroform. The combined organic extracts were washed well with water, dried (MgSO$_4$) and evaporated in vacuo to afford an orange oil (3.16g). This oil, in ethanol (15ml), was treated with a slight excess of ethanolic hydrogen chloride, ether was added and the precipitated hydrochloride collected by filtration and recrystallized from ethanol-ether to afford title compound (1.4g) m.p. above 300° after a change of crystalline form about 260°. (Found: C,74.4; H,9.1; Cl,12.2; N,4.65. C$_{18}$H$_{26}$ClN requires C,74.1; H,9.0; Cl,12.15; N,4.8%).

EXAMPLE 26

10-Allylaminobornane hydrobromide

A solution of 10-bornanamine (obtained by basification, with sodium hydroxide, of 1.517g. 10-bornanamine hydrochloride) in acetone (20ml) containing allyl bromide (0.68ml) was kept at room temperature for 3.5 days during which time a small amount of solid crystallized. The solution was evaporated to about one third of its original volume, cooled to 0° and the crystalline material collected by filtration to give title compound m.p. above 295° with slow decomp. (Found: C,56.6; H,8.6; N,5.1. C$_{13}$H$_{24}$BrN requires C,56.95; H,8.8; N,5.1%).

EXAMPLE 27

1,3,5-Tris-(bornan-10-yl)-hexahydro-1,3,5-triazine

10-Bornanamine (824mg) in benzene (10ml) was treated with formaldehyde (37%; 0.44ml) and the mixture was stirred at room temperature for 1 hour. A crushed pellet of sodium hydroxide was added to the heterogeneous mixture which was then separated from the aqueous layer. Evaporation of the solvent in vacuo afforded a crystalline solid which was recrystallized from ether-methanol to give title compound (490mg) m.p. 175°–180° (sealed cap.) (Found: C,79.7; H,11.4; N,8.25. C$_{33}$H$_{57}$N$_3$ requires C,79.9; H,11.6; N,8.45%).

EXAMPLE 28

10-Benzylaminobornane hydrochloride

10-Bornanamine (824mg) in toluene (20ml) was treated with benzaldehyde (0.55ml) and the solution refluxed under nitrogen under a Dean and Stark water trap for four days. Evaporation of the solvent in vacuo afforded impure 10-benzylidene-10-bornanamine which was dissolved in dimethoxyethane (10ml) containing lithium aluminium hydride (112mg.). The resulting mixture was refluxed for 2.25 hours, cooled, and the excess hydride decomposed by the addition of water. The precipitated inorganic material was removed by filtration and the solvent was evaporated in vacuo. The residual gum was triturated with 2N-hydrochloric acid to afford an insoluble hydrochloride which was collected by filtration and then partitioned between ether and 2N-sodium hydroxide. The dried ethereal layer was evaporated in vacuo to give a yellow oil which was dissolved in ether and treated with ethanolic hydrogen chloride. The precipitated solid was collected and recrystallized from water to give title compound m.p. 310° (Found: C, 72.65; H, 9.65; Cl, 13.3; N, 4.95. C$_{17}$H$_{26}$ClN requires C, 72.95; H, 9.35; Cl, 12.65; N, 5.0%).

EXAMPLE 29

1-Dimethylamino-7,7-dimethylnorbornane hydrochloride

A mixture of 1-amino-7,7-dimethylnorbornane (71 5mg), formic acid (98%, 1.4 ml) and formaldehyde (37%, 2.4 ml) was heated on the steam bath for 15.5 hours. The cooled solution was poured into 2N-sodium hydroxide solution and extracted with ether. The washed extract was evaporated to give a mobile oil which was dissolved in ether and treated with a slight excess of ethanolic hydrogen chloride. The precipitated hydrochloride was collected by filtration and recrystallized from ethanol-ether to afford title compound (627 mg), sublimes above 150°, m.p. 208°–209°. (Found: C, 64.75; H, 10.85; Cl, 17.5; N, 6.7. C$_{11}$H$_{22}$ClN requires C, 64.85; H, 10.9; Cl, 17.4; N, 6.7%).

EXAMPLE 30

7,7-Dimethyl-1-morpholinonorbornane hydrochloride

A stirred mixture of 1-amino-7,7-dimethylnorbornane (0.7 gm) potassium carbonate (0.77 gm) and 2,2'-dichlorodiethyl ether (3 ml) was heated at 130° for 2 hrs. The reaction mixture was then cooled and partitioned between ether and 2 N hydrochloric acid solution. The aqueous layer was separated basified and extracted into ether. The organic layer was dried, and evaporated. The residue (0.8 gm) after purification by chromatography was dissolved in dry ether and treated with hydrogen chloride to give the title compound (0.33 gm) m.p. 243° to 246°.

EXAMPLE A

| Tablet. | |
|---|---|
| 7,7-dimethylnorbornan-1-amine-hydrochloride | 250 mg |
| Lactose | 30 mg |
| Gum Acacia | 15 mg |
| Magnesium stearate | 5 mg |

Sufficient water is added to the active ingredient to form a granulating fluid and the pH adjusted to about 5.0 with the aid of citric acid. The gum acacia is dissolved in and this solution used to granulate the lactose. The ingredients are then passed through a 20 mesh (B.S.) sieve, dried, lubricated with the magnesium stearate and compressed.

EXAMPLE B

| Injection | |
|---|---|
| Antiviral compound | 1.0% w/v |
| Sodium chloride | 0.80% |
| Water for Injection | to 100% |

Dissolve the sodium chloride and antiviral compound in water for injection. Make up to volume and mix. Filter and then fill into ampoules which are then sealed and sterilized by autoclaving.

Similarly preparations having 2.0% w/v antiviral compound can be prepared.

EXAMPLE C

| Eye Drops | |
|---|---|
| Antiviral compound | 2.0% w/v |
| Propylene glycol | 5.0% |
| Sodium chloride | 0.6% |
| Sodium edetate | 0.01% |
| Thiomersal | 0.01% |
| Methyl p-hydroxy benzoate | 0.03% |
| Propyl p-hydroxy benzoate | 0.02% |
| Butyl p-hydroxy benzoate | 0.01% |
| Distilled Water | to 100.0% |

Dissolve the para hydroxy benzoates in the propylene gylcol and add the solution to water; mix. Add and dissolve the thiomersal, sodium chloride and antiviral compound. Make up to volume and mix. Sterilize the solution by filtration and fill aseptically into polythene eye drop bottles previously sterilized by δ-radiation.

EXAMPLE D

| Nasal Drops | |
|---|---|
| Antiviral compound | 2.0% w/v |
| Chlorbutol | 0.5% |
| Sodium chloride | 0.7% |
| Distilled Water | to 100% |

Dissolve the chlorbutol in water, heating to 60° C. Cool and add the sodium chloride and antiviral compound. Make up to volume, clarify by filtration and fill into suitable glass bottles fitted with a dropper.

EXAMPLE E

| Nasal Aerosol | |
|---|---|
| Example (i) (for doses of 1000 μg) | |
| Antiviral compound | 1.17% w/w |
| Ethanol | 30% |
| Dichlorodifluoromethane | 35% |
| Dichlorotetrafluoroethane | to 100% |

Dissolve the antiviral compound in the ethanol. Fill the required quantity of this solution into aluminium aerosol cans or plastic coated glass aerosol bottles, seal with a metered valve delivering 85 mg per burst and pressurize by forcing through the valve the required quantity of the required mixture of dichlorodifluoromethane and dichlorotetrafluoroethane.

| Example (ii) (for doses of 1 mg) | |
|---|---|
| Antiviral compound | 1.17% w/w |
| Sorbitan trioleate | 0.59% w/w |
| Dichlorodifluoromethane | 50.0% |
| Trichlorofluoromethane | to 100% |

Micronize the antiviral compound. Mix the sorbitan trioleate with the trichlorofluoromethane (cooled to +10° C) and dispense the antiviral compound into the mixture. Fill the required quantity of this mixture into cans (as above), fit the valve (as above) and pressurize with dichlorodifluoromethane (as above).

EXAMPLE F

| Inhalation Aerosol | |
|---|---|
| Example (i) (doses of 1 mg) | |
| Antiviral compound | 1.17% w/w |
| Dichlorodifluoromethane | 70% |
| Ethanol | to 100% |

Method
EITHER
Dissolve the antiviral compound in the alcohol. Add the solution to the dichlorodifluoromethane (cooled to −50° C). Mix and fill into aerosol bottles or cans and seal with valves (as above for nasal aerosols).
OR
Dissolve the antiviral compound in the alcohol. Fill the required quantity into bottles or cans (as above) and seal with suitable metering valves (as above). Pressurized (as above) with the required quantity of dichlorodifluoromethane.

| Example (ii) (for doses of 1 mg) | |
|---|---|
| Antiviral compound | 1.17% w/w |
| Sorbitan trioleate | 0.59% |
| Dichlorodifluoromethane | 70.0% |
| Trichlorofluoromethane | to 100.0% |

Method - as Example E (ii)

EXAMPLE G

| Suppository | |
|---|---|
| Antiviral compound | 200 mg |
| *Suppository base | to 2.0 grams |

*This can be selected from a wide variety of natural and proprietary semi-synthetic bases Micronize the antiviral compound and disperse in the molten suppository base (at 50° C). Cool to 35°–37° C and fill into suitable suppository moulds.

I claim:
1. A pharmaceutical composition for treating viral infections and disorders of the central nervous system comprising a pharmaceutical carrier or excipient and a therapeutically effective amount of a 7,7-dimethyl-[2,2,1]-bicycloheptane having at the 1-position a group R, where R is an amino or aminomethyl group, or a derivative of said amino or aminomethyl group wherein R is substituted at at least the amino nitrogen atom or at the 10-carbon atom by one or more $C_{1-6}$ aliphatic, $C_{3-10}$ cycloaliphatic, benzyl, styryl, phenylethynyl or phenyl groups; or a physiologically acceptable salt thereof.

2. A composition as claimed in claim 1 in dosage unit form.

3. A composition as claimed in claim 2 in which each dosage unit contains 0.05 g to 4 g active material.

4. A composition as claimed in claim 2 in which each dosage unit contains 0.025 g to 4 g active material.

5. A composition as claimed in claim 1 suitable for administration as a nasal spray or nasal drops, or in the form of an aerosol for inhalation.

6. A composition as claimed in claim 1 wherein R is an amino or substituted amino group.

7. A composition as claimed in claim 1 wherein R is an aminomethyl or substituted aminomethyl group.

8. A composition as claimed in claim 6 wherein R is a $C_{1-6}$ mono- or dialkylamino group.

9. A composition as claimed in claim 7 wherein R is an aminomethyl, a $C_{1-6}$ mono- or dialkyl- or alkenyl-aminomethyl or 1-aminoethyl group.

10. A composition as claimed in claim 1 wherein R is an aminomethyl group or the monomethyl, monoethyl, monallyl, mono-n-butyl, dimethyl or diethyl amino-substituted derivatives thereof, or 1-aminoethyl group.

11. A composition as claimed in claim 1 wherein R is an amino, methylamino, ethylamino or dimethylamino group.

12. A method of treating viral infections and disorders of the central nervous system in animals including man which comprises administering to the animal a composition as claimed in claim 1.

13. A composition as claimed in claim 1 wherein R is substituted by alkyl, alkenyl or alkynyl group of up to 6 carbon atoms, which may be unsubstituted or substituted by an amino, $C_{1-6}$ mono- or dialkylamino, imino, hydroxy, thiol, an esterified or etherified hydroxy or thiol group or, when a basic grouping is also present on the group, an oxo group in an alpha-position in relation to the 1- or 10-nitrogen atom; a $C_{3-8}$ cycloalkyl group; benzyl, styryl, phenylethynyl or a phenyl group.

14. 7,7-dimethyl-[2,2,1]-2-bicycloheptanes having at the 1-position a group R and the physiologically acceptable salts thereof, wherein R is an amino or aminomethyl group possessing a basic nitrogen atom and is substituted at at least the amino nitrogen atom or at the 10-carbon atom by one or more $C_{1-6}$ aliphatic, $C_{3-10}$ cycloaliphatic, benzyl, styryl, phenylethynyl, or phenyl groups.

15. A process for the preparation of a compound as claimed in claim 14:
(a) wherein the R group possesses a methylene group in an alpha-position in relation to the nitrogen atom, which comprises reducing the corresponding amide;
(b) wherein R is a methylamino group, which comprises reducing an ester of the corresponding carboxyamino compound;
(c) wherein R is a methylamino group, which comprises reductively methylating the corresponding amine;
(d) wherein the nitrogen atom of R is linked by a double bond to a $C_{1-6}$ aliphatic, benzyl, styryl, phenylethynyl, which comprises condensing the corresponding amine with an aldehyde or ketone;
(e) wherein R is an aminomethyl group in which one of the hydrogen atoms on the methyl carbon atom is substituted, which comprises reducing the corresponding ketoxamine;
(f) wherein the nitrogen atom of R bears an phenyl substituent, which comprises reacting the corresponding amine with a benzyne;
(g) wherein the nitrogen atom of R is substituted by a $C_{1-6}$ aliphatic, $C_{3-10}$ cycloaliphatic, benzyl, styryl or phenylethynyl group, which comprises reacting the corresponding amine with a compound of formula $R^5X$ where $R^5$ is a $C_{1-6}$ aliphatic, $C_{3-10}$ cycloaliphatic, or benzyl, styryl or phenylethynyl group, and X is a readily eliminatable group;
(h) where R is an aminomethyl group in which the methyl group is substituted, which comprises reducing the corresponding substituted nitromethyl compound;
(i) wherein the nitrogen atom of R is substituted by an aminoacyl group which comprises reacting a corresponding haloacyl compound with ammonia or an amine; or
(j) wherein the nitrogen atom of R is substituted by $C_{1-6}$ aliphatic or benzyl, styryl or phenylethynyl group, which comprises reducing the corresponding compound in which the said nitrogen atom is linked to said group by a double bond.

* * * * *